United States Patent [19]

Merkatoris et al.

[11] Patent Number: 5,000,806
[45] Date of Patent: Mar. 19, 1991

[54] METHOD AND APPARATUS FOR APPLYING AN ELASTIC STRAND TO A DISPOSABLE DIAPER

[75] Inventors: John R. Merkatoris; James E. Hertel; Dale E. Zeman, all of Green Bay, Wis.

[73] Assignee: Paper Converting Machine Company, Green Bay, Wis.

[21] Appl. No.: 406,560

[22] Filed: Sep. 13, 1989

Related U.S. Application Data

[63] Continuation-in-part of Ser. No. 183,060, Apr. 19, 1988.

[51] Int. Cl.$^5$ .................. B32B 31/18; B65H 59/32
[52] U.S. Cl. .......................... 156/161; 26/52; 28/102; 28/244; 28/245; 156/164; 156/229; 156/494; 156/519; 156/521; 156/552; 156/567
[58] Field of Search .................. 28/244, 245, 243, 240, 28/102; 26/52, 53, 51, 51.3, 77, 88, 90; 156/161, 163, 164, 177, 179, 229, 265, 303, 434, 439, 494, 495, 496, 519, 552, 568

[56] References Cited

U.S. PATENT DOCUMENTS

| | | | |
|---|---|---|---|
| 30,801 | 12/1860 | Cleveland | 26/90 |
| 485,400 | 11/1892 | Watson | 26/90 X |
| 1,014,916 | 1/1912 | Stevens | 156/439 |
| 2,483,339 | 9/1949 | Gardner et al. | 26/87 |
| 2,702,406 | 2/1955 | Reed | 26/88 X |
| 3,179,348 | 4/1965 | Nystrand et al. | 242/56 |
| 3,444,020 | 5/1969 | Kalwaites | 156/177 X |
| 3,639,917 | 2/1972 | Althouse | 2/270 |
| 3,728,191 | 4/1973 | Wierzba et al. | 156/265 |
| 3,805,341 | 4/1974 | Jense | 156/439 X |
| 4,227,952 | 10/1980 | Sabee | 156/164 |
| 4,284,454 | 8/1981 | Joa | 156/229 X |
| 4,349,195 | 9/1982 | Small et al. | 270/32 |
| 4,360,398 | 11/1982 | Sabee | 156/164 |
| 4,364,787 | 12/1982 | Radzins | 156/164 |
| 4,494,740 | 1/1985 | Noboru et al. | 26/90 X |
| 4,523,969 | 6/1985 | Spencer | 156/161 |
| 4,573,991 | 3/1986 | Pieniak et al. | 604/385.2 |
| 4,608,115 | 8/1986 | Schroth et al. | 156/164 |
| 4,642,150 | 2/1987 | Stemmler | 156/164 |
| 4,726,874 | 2/1988 | VanVliet | 156/495 |
| 4,735,673 | 4/1988 | Piron | 156/496 |
| 4,776,911 | 10/1988 | Uda et al. | 156/164 |
| 4,925,520 | 5/1990 | Beaudoin et al. | 156/164 |

FOREIGN PATENT DOCUMENTS

| | | |
|---|---|---|
| 0139620 | 2/1985 | European Pat. Off. . |
| 0159627 | 10/1985 | European Pat. Off. . |
| 0236032 | 9/1987 | European Pat. Off. . |
| 0338662 | 10/1989 | European Pat. Off. . |
| 2492310 | 4/1982 | France . |

Primary Examiner—Michael L. Lewis
Attorney, Agent, or Firm—Tilton, Fallon, Lungmus & Chestnut

[57] ABSTRACT

The invention includes a method and apparatus for applying an elastic strand to disposable diapers. It uses canted, spindle-equipped wheels for engaging an elastic strand, moving the elastic strand into a sinuous configuration and stretching the strand. Stripping belts apply the strand to a diaper component.

15 Claims, 3 Drawing Sheets

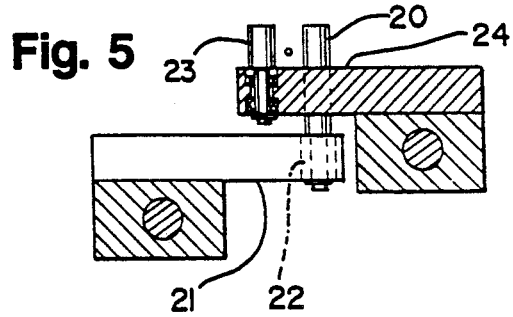
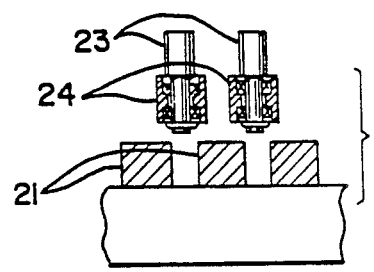
Fig. 5
Fig. 6
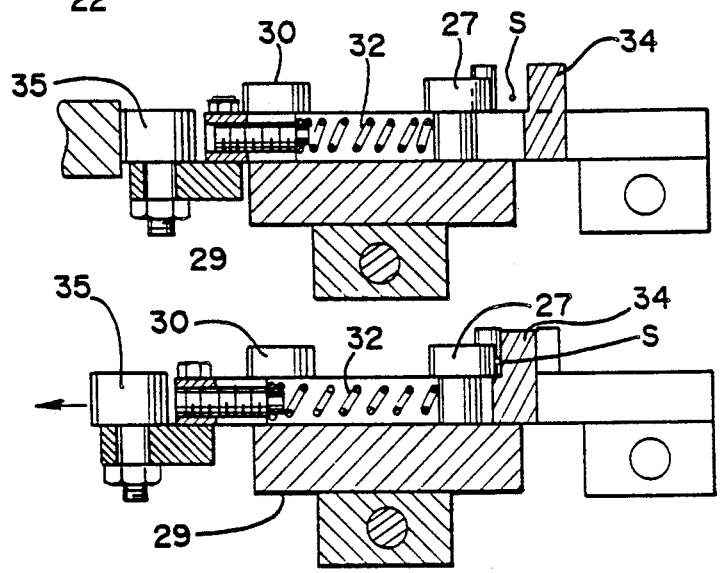
Fig. 7
Fig. 8
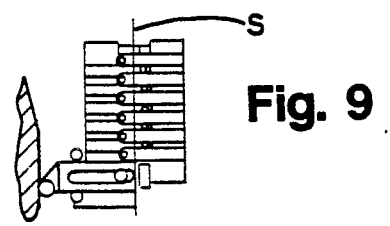
Fig. 9
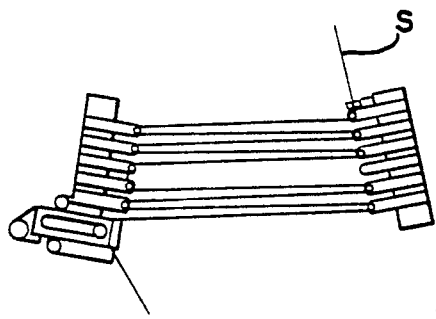
Fig. 10
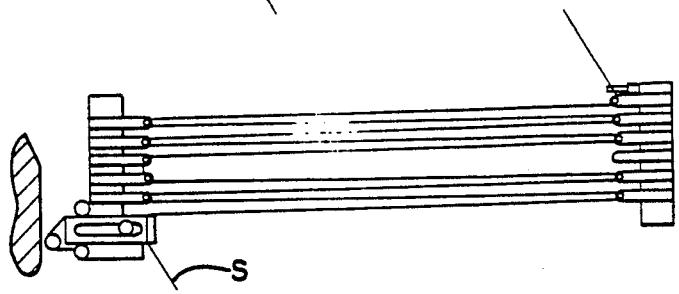
Fig. 11

METHOD AND APPARATUS FOR APPLYING AN ELASTIC STRAND TO A DISPOSABLE DIAPER

BACKGROUND OF THE INVENTION

This application is a continuation-in-part of application Ser. No. 183,060, filed Apr. 19, 1988 for a "Method And Apparatus For Applying An Elastic Waistband To A Disposable Diaper."

FIELD OF THE INVENTION

This invention relates to a method and apparatus for applying an elastic strand to a disposable diaper and, more particularly, to a unique method and apparatus for bending the strand into a sinuous configuration, stretching it and applying it to a diaper component to develop the necessary gathering in the final diaper product.

DESCRIPTION OF THE PRIOR ART

Disposable diapers typically include a moisture-pervious layer (non-woven) for positioning adjacent the body of an infant, an outer layer of moisture-impervious material, e.g., polyethylene, and an absorbent batt disposed between these two layers. These diapers also include elastic leg and waistbands fixedly secured to the layers of the diaper. The elastic bands gather the material around the waist and leg openings of the diaper and allow a user to secure the diaper snugly on an infant.

The prior art includes a wide variety of machines and methods used to produce disposable diapers. Some of these prior machines secure the elastic bands to the diaper and then heat-shrink the band to develop the necessary gathering at the waist or leg opening. To heat the elastic, these prior machines use complicated mechanisms which reduce the speed of operation of the machine. The reduction in speed and the added cost of using exotic elastic materials and procedures substantially increases the cost of the resulting diaper.

Other prior machines stretch elastic bands made out of materials such as polyurethane foam and then secure the bands to the material layers of a diaper. These machines use complicated mechanisms to stretch the elastic material and adhere or otherwise secure it to the layers or webs of the diaper. In addition, these mechanisms require the use of substantial amounts of elastic materials. Finally, the complexities of these mechanisms and the amount of material required also unduly increases the cost of the diaper that these machines and methods produce.

The apparatus of the present invention is of simple construction which bends an elastic strand of material into a sinuous configuration, stretches this sinuous strand and applies it to a web of a disposable diaper. It produces this result with a simple, high-speed, rotary operation which minimizes the cost of operation and requires a small amount of elastic material. Accordingly, the apparatus and method of the present invention minimizes the cost of producing the resulting diaper.

SUMMARY OF THE INVENTION

In accordance with one embodiment of this invention, a pair of canted wheels include at least one set of spindles on each of their peripheries. These wheels rotate and move their spindles into a staggered or "nested" configuration at a first position on opposite sides of a strand of elastic material. In contrast to the above mentioned application Ser. No. 183,060, the spindles here do not impale the elastic material but rather flank it. As the wheels rotate, the spindles engage the strand, move it into a sinuous configuration between the wheels, and stretch it. Due to the cant in the wheels, the corresponding sets of spindles move farther apart as the wheels rotate away from the first position.

The wheels move the elastic strand to a second position where a first and second continuous belt deposit it onto a web used to construct diapers They deposit the elastic strand on a portion of the web which receives adhesive before receiving the strand. A supporting roll supports the web while the web receives the elastic strand. This supporting roll co-acts with the belts to apply pressure to the edge portions of the stretched elastic strand outside of the area with adhesive and insure that the adhesive secures the strand to the web. After the belts have stripped the elastic strand off of the spindles of the canted wheels and clamped it on the web, a knife cuts the trailing end of the strand.

While the supporting roll supports the web and the stretched elastic strand, the belts apply pressure to the edge portions of the strand to prevent the strand from contracting to its relaxed state and to insure that the strand adheres to the web. They provide this pressure for a predetermined time period—a period sufficiently long to insure a permanent adhesive bond between the elastic strand and the web. The supporting roll continues to support the web with the strand of elastic material on it until the web unites with other components.

BRIEF DESCRIPTION OF THE DRAWINGS

For a more complete understanding of this invention, one should now refer to the embodiment illustrated in greater detail in the accompanying drawings and described below by way of an example of the invention. In the drawings:

FIG. 5 is a sectional view taken along line 5—5 in FIG. 4;

FIG. 6 is a sectional view taken along line 6—6 in FIG. 4;

FIG. 7 is a sectional view taken along line 7—7 in FIG. 4 showing the clamp used to secure the elastic strand in its open position;

FIG. 8 is the sectional view of FIG. 7 showing the clamp in the closed position;

FIG. 9 is a schematic diagram of corresponding sets of spindles on the canted wheels disposed in the first position;

FIG. 10 is a schematic diagram of the spindles shown in FIG. 9 after the canted wheels have rotated away from the first position; and FIG. 11 is a schematic diagram of the spindles of FIG. 9 after they have moved to a second position.

While the following disclosure describes the invention in connection with one embodiment, one should understand that the invention is not limited to this embodiment. Furthermore, one should understand that the drawings are not necessarily to scale and that the embodiment is illustrated, in part, by graphic symbols, diagrammatic representations, and fragmentary views.

In certain instances, the disclosure may not include details which are not necessary for an understanding of the present invention, such as conventional details of fabrication and assembly.

DETAILED DESCRIPTION OF THE DRAWINGS AND AN EMBODIMENT

Figure 1:
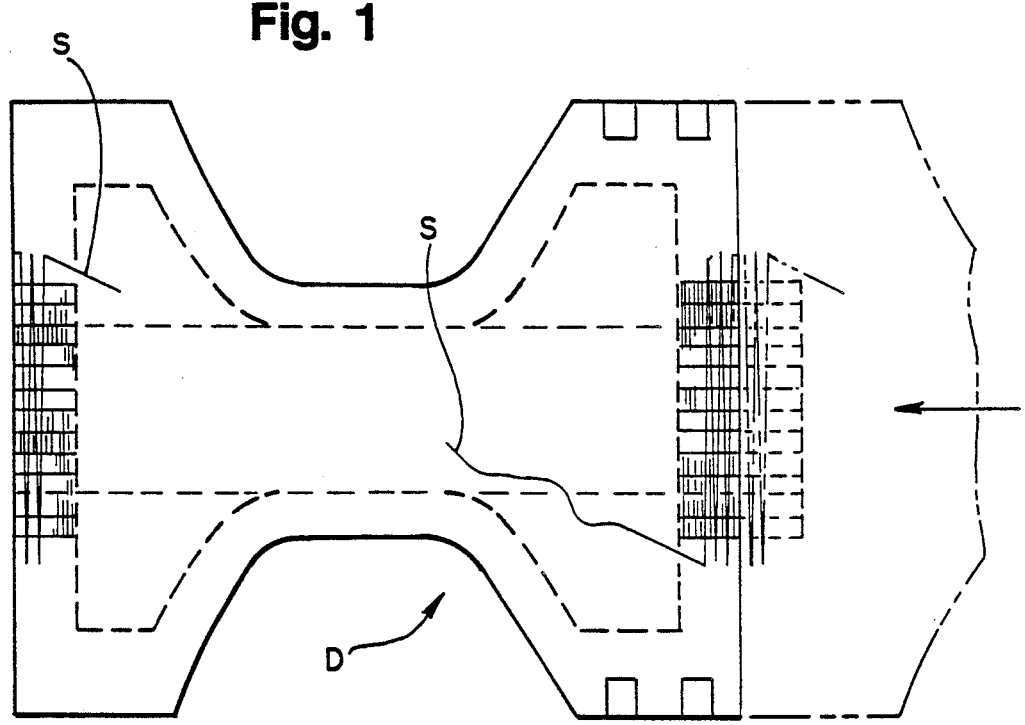
FIG. 1 is a top plan view of he diaper produced by the apparatus and method of the present invention.
Figure 2:
FIG. 2 is a side elevation view (essentially schematic) of the apparatus of the present invention.
Figure 3:
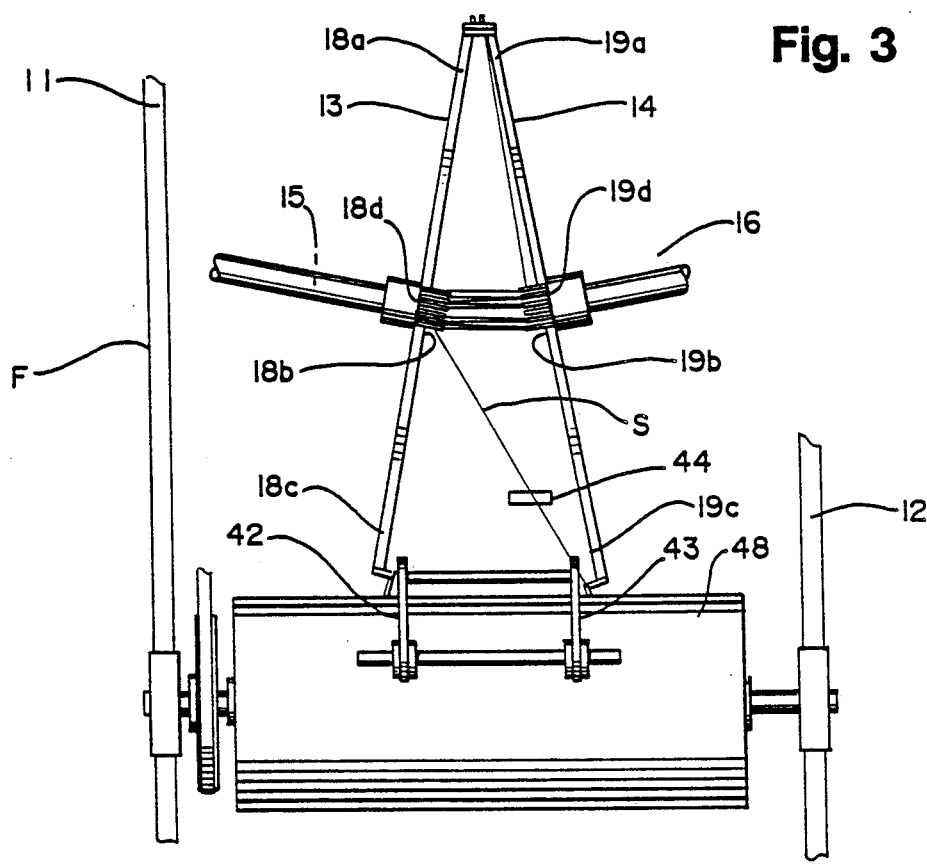
FIG. 3 is a sectional view taken along line 3—3 in FIG. 2.

Turning now to the drawings and referring first to FIGS. 1—3, the apparatus of the present invention shown generally at 10 (See FIG. 2) produces diapers D (See FIG. 1) with elastic strands S disposed in a sinuous configuration and adhesively secured to the waist area of the diaper. The strand S is a material produced and marketed by E. I. DuPont de Nemours & Co. under the trademark LYCRA. Alternatively, it may be any other suitable elastic strand. The apparatus 10 includes a frame F (See FIG. 3) with a pair of side frames 11 and 12 united by suitable cross-members (not shown). This frame F defines the path of operation of the apparatus 10.

The frame F rotatably supports a pair of canted wheels 13 and 14 which lie in transversely spaced-apart relation for rotation about angularly related axes as at 15 relative to the wheel 13 and as at 16 relative to the wheel 14. A drive (not shown) moves the wheels 13 and 14 which have the same general configuration. The wheel 13 includes a hub 17 and four circumferentially spaced spoke segments 18a, 18b, 18c, and 18d spaced 90° apart. Similarly, wheel 14 has a hub and spoke segments 19a, 19b, 19c, and 19d which correspond to segments 18a-d, respectively.

Each spoke of the wheels 13 and 14 supports a plurality of spindles. Moreover, the spokes 18a-d each support the same set of components, as described below; and the spokes 19a-d each support the same set of components, a set different from the one supported by the spokes 18a-d. For example, the spoke 18a of the wheel 13 supports spindles 20 (See FIG. 4). The spindles 20 lie inwardly of the inner face of wheel 13, i.e., toward the wheel 14, and extend generally radially of the wheel 13 in equally spaced relation to form a row. Axially-extending support arms 21 rotatably mount each spindle 20 to the spoke 18a, i.e., each spindle 20 rotates within a bearing 22 disposed in a suitably sized opening in the arm 21 (See FIG. 5).

Figure 4:
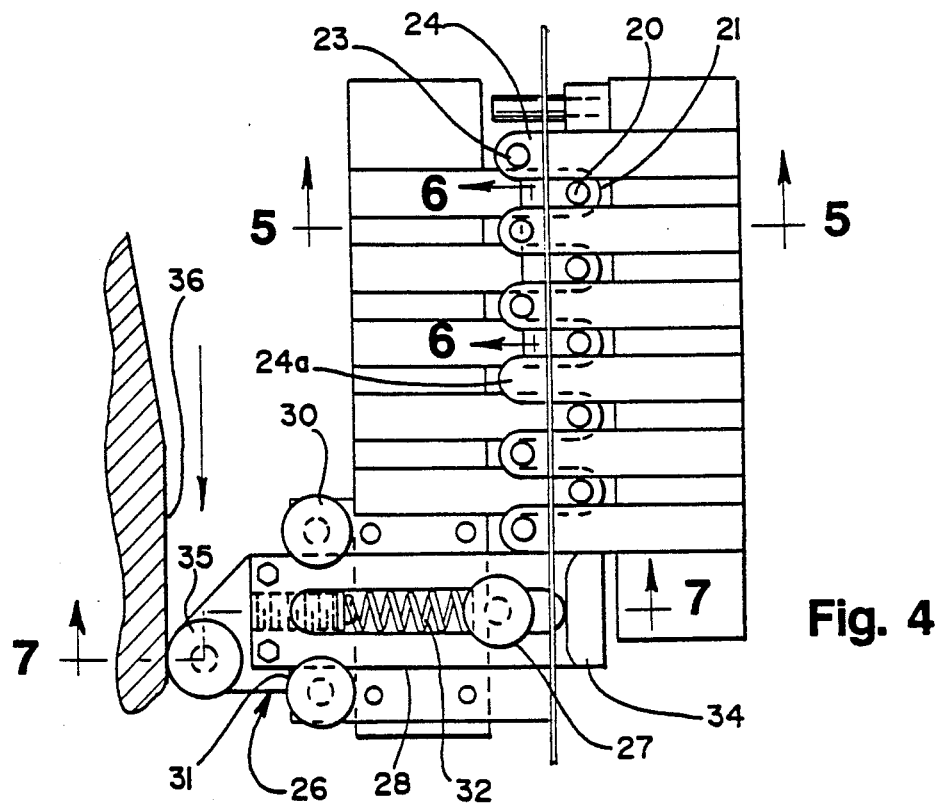
FIG. 4 is a top plan view of corresponding sets of spindles disposed on the two canted wheels in staggered relation at a first position.

Similarly, spoke 19a of the wheel 14 includes spindles 23 secured to the spoke 19a with support arm 24 (See FIGS. 4 an 5). The spindles 23 lie inwardly of the inner face of wheel 14, i.e., toward the wheel 13. They extend generally radially of the wheel 14 in equally spaced relation to form a row. Each spindle 23 rotates within a bearing 25 disposed in a suitably sized opening in the support arm 24. The configuration shown in FIG. 4 does not include one of the spindles 23 (on the arm 24a) for the reason set forth below.

As shown in the lower left hand portion of FIG. 4, each spoke segment 18a-d also includes a clamp 26 with a stationary stop member 27; a movable clamping member 28 disposed in sliding engagement with a base 29 (See FIG. 7) between two guide bolts 30 and 31; and a spring 32 which biases the clamping member 28 against the stop member 27. The clamping member 28 includes an elongate slot 33, a stop engaging portion 34 and a cam follower 35. The stop 27 extends through the slot 33 at one end of the slot; and the spring 32 lies in the slot 33 between the stop 27 and a compression adjusting screw threaded into the clamping member 28 at the opposite end of the slot.

The spring 32 biases the clamping member to the left in FIG. 4 and forces the stop engaging portion 34 against the stop 27 or the strand S when it lies between the stop and the stop engaging portion. Thus, the clamp 26 secures the strand to the wheel 13 (See FIG. 8). To move the portion 34 out of engagement with the stop 27 (or the strand S) and provide a gap between the stop and the portion 34, the cam follower co-acts with a stationary camming surface 36, moving the clamping member 28 to the right in FIG. 4 and overcoming the force of the spring 32 (See FIG. 7).

Although the illustrated embodiment includes one clamp mechanism on each spoke 18a-d for clamping the strand forwardly of the spindles, the wheels may include clamps for clamping the strand rearwardly of the spindles. Furthermore, the wheels may include clamps for clamping both the strand both forwardly and rearwardly of the spindles As shown in FIG. 2, the wheels 13 and 14 rotate counterclockwise. As they move to a first location at 37, the spindles 20 and 23 "nest" as shown in FIG. 4, i.e., move into a staggered relation on opposite sides of the strand S. (A supply roll 38 provides the strand S.) In addition, the cam follower 35 of the clamping member 28 engages the stationary camming surface 36 on the frame F. As the wheels rotate and the cam follower moves over the camming surface, the clamping member 28 slides towards the wheel 14; and the stop engaging portion 34 moves away from the stop 27 against the force of the spring 32.

After the wheels have rotated sufficiently to place the spindles 20 and 23 in the arrangement shown in FIG. 4, the cam follower 35 releases from the camming surface, and the stop engaging portion 34 clamps the strand S against the stop 27 (See FIG. 8) to secure the strand to the wheel 13 forwardly—in the direction of wheel rotation—of the spindles 20 (See FIG. 9). As the wheels 13 and 14 continue to rotate from the location 37 through the location 39 to the location 40, their peripheries move apart. Consequently, the spindles 20 and 23 engage the strand S and force it to follow a sinuous path between them as shown in FIG. 10.

The supply roll 38 provides more elastic strand as the wheels move farther apart. This additional strand is not sufficient to prevent stretching of the strand disposed between the pins from stretching because of (1) the speed of the wheels 13 and 14, and (2) the clamping of the trailing end of the strand by the next spoke. Thus, the wheels stretch the strand S as it moves in a sinuous path between the spindles 20 and 23. To facilitate the movement of the strand between them, the spindles rotate.

At a location 40, having rotated 180° from the location 37, the wheels 13 and 14 place the strand S into alignment with the path of travel of a non-woven web 41. A pair of endless belts 42 and 43 (See FIG. 3) transfer the strand S transversely to the non-woven web 41 which a parent roll (not shown) provides. As the strand transfers to the non-woven web 41, a knife 44 cuts the back end of the strand S. The knife 44 is stationary, secured between the wheels 13 and 14 by suitable supports. Alteratively, the apparatus 10 may include knife means disposed on the wheels 13 and/or 14. Before the knife 44 cuts the strand S, a clamp 26 of the following spoke clamps the strand S to continue the operation outlined above.

A set of pulleys 45, 46 and 47 mounted for rotation within the frame F support the belt 42; and a set of corresponding pulleys, similarly mounted for rotation within the frame F, support the belt 43. Although the illustrated embodiment includes two belts, it may include only one belt which extends across the space between the belts 42 and 43 in the illustrated embodiment—or a plurality of belts spaced across this space. However, these alternatives require the use of adhesive which has a greater affinity for the web 41 and strand S than for the belts.

The belts 42 and 43 cooperate with a supporting roll 48 (also rotatably mounted in the frame F) to provide pressure to the edge portions of the stretched elastic strand S. They prevent the strand from contracting to its relaxed state and insure that the strand S adheres to the web 41. The belts provide pressure for a predetermined time period (i.e., along approximately one half of the circumference of the roll 48)—a period sufficient to insure a permanent adhesive bond between the stretched elastic strand and the web.

An adhesive applying unit 49 applies longitudinally spaced-apart bands or areas of adhesive to web 41 where the web later receives strands. This unit 49 applies the adhesive to the web 41 before the web moves to the location 40 (the stripping area). However, the apparatus 10 may have an adhesive unit at the location 40 rather than at the location shown in FIG. 2.

The supporting roll 48 supports the web 41 and moves it past the belts 42 and 43 to a nip 50 defined by the supporting roll 48 and a guide roll 51. The web 41 with a stretched strand S fixedly secured to it unites with spaced-apart batts 52 and a moisture-impervious web 53 (e.q., polyethylene) at the nip 50. A chill roll 54 advances the web 53 to the nip 50 and an adhesive applying unit 55 applies longitudinally spaced-apart areas of adhesive to the web 53 at the roll 54. These areas of adhesive register with the stretched elastic strand S and secure it to the web 53 at the nip 50.

Conveyor belts as at 56 and 57 advance the batts 52 to the nip 50; and a fine line glue assembly 58 applies longitudinally spaced-apart glue lines to the web 53. These glue lines register with the batts 52 and secure the batts 52 and the web 53 together at the nip 50. The composite diaper structure then moves past the nip 50 down the production line (to the left in FIG. 2); and a cutting apparatus 59 cuts and severs the now-combined webs 41 and 53 to form a series of discrete diapers D.

In the illustrated embodiment, the canted wheels apply a strand segment to the web 41 at predetermined intervals to install one strand segment per diaper. The strand pattern spans the leading edge of one diaper and the trailing edge of the preceding diaper (See FIG. 1). The transverse severing which forms discrete diapers occurs midway of the strand pattern along the enlarged gap provided by the missing spindle 23 at the position 24a (See FIG. 9).

In operation, the wheels 13 and 14 rotate counterclockwise and nest their spindles at 37. There, the spindles 20 of the wheel 13 move into a position on one side of an elastic strip S and the spindles 23 of the wheel 14 move on the other side of the strand S. The clamp 26 secures the leading end of the strand S to the wheel 13. As the wheels continue to rotate, their peripheries move apart and the pins 20 and 23 engage the strand and move it into a sinuous configuration. The wheels move farther apart as they rotate and stretch the strand.

The next set of spokes reach the location 37 and clamp the trailing end of the strand S. This clamping allows further stretching of the strand portion disposed around the spindles of the spokes which have moved away from the location 37. At the location 40, the belts 42 and 43 strip the strand from the spindles and deposit the stretched and patterned strand onto the web 41 on adhesive previously applied by the adhesive unit 49. The belts also apply pressure to insure that the strand S adheres to the web. As the belts strip the strand S, the cam follower 35 of the clamp 26 co-acts with another camming surface to release the strand S.

At the nip 50, the web 41 unites with the batts 52 and the web 53 while the roll 48 continues to support the web 41. A composite diaper structure forms at the nip 50 and moves down the production line. Then the apparatus 59 cuts and severs the composite diaper structure to form a series of discrete diapers D shown in FIG. 1.

While the above description and the drawings disclose one embodiment, one should understand, of course, that the invention is not limited to this embodiment. Those skilled in the art to which the invention pertains may make modifications and other embodiments employing the principles of this invention, particularly upon considering the foregoing teachings.

For example, one may set the sequence of feeding the strand S and stretching it to provide strand feeding for the first 90° rotation from the strand "pickup" point (location 37) and strand stretching for the following 90 rotation. In addition, one may modify the apparatus 10 to include means for providing a second non-woven web at 40. This second web would travel over the belts 42 and 43 and around the pulley 45 which supports the belt 42 and the corresponding pulley which supports the belt 43. For this alternative, the pulley 45 (and the corresponding pulley for belt 43) would have a width sufficient to support the second non-woven web. Therefore, by the appended claims, the applicants intend to cover any modifications and other embodiments which incorporate those features which constitute the essential features of this invention.

What is claimed is:

1. An apparatus for making disposable diapers having a stretchable waist, said apparatus comprising:
    a frame;
    a pair of spaced-apart wheels mounted on said frame for rotation about angularly related axes whereby corresponding points on the peripheries of said wheels are closer together at a first position than at a second position, said second position being spaced circumferentially from said first position;
    spindle means disposed on the periphery of each of said wheels for receiving an elastic strand and placing said strand into a stretched, sinuous configuration upon wheel rotation from said first to said second position, the spindle means of one wheel interleaving with the spindle means of the other wheel at the first position so that the spindle means may receive the strand at the first position and move adjacent portions of the strand in opposite directions as the wheels rotate away from the first position;
    and transfer means disposed on said frame for removing said elastic strand from said spindle means at a second position, adhesively and substantially simultaneously uniting said elastic material to a diaper component web, and applying a pressure for a predetermined duration to allow the bond between the elastic material and the diaper component web to develop.

2. The apparatus of claim 1, wherein said spindle means includes at least one set of spindles rotatably mounted on one wheel in spaced relation along the periphery of said one wheel and at least one set of spindles rotatably mounted on the other wheel in spaced relation along the periphery of said other wheel.

3. The apparatus of claim 2, wherein said wheels include a support arm for each spindle, each spindle being rotatably mounted to one end of a corresponding support arm, the other opposite end of said corresponding support arm being fixedly secured to a wheel, said one end of said support arm being disposed outwardly of the wheel to which it is fixedly secured toward said other wheel.

4. The apparatus of claim 3, wherein at said first location said set of spindles of one wheel lie in staggered relation with the set of spindles of the other wheel and each set of spindles being disposed between the other set of spindles and the wheel on which said other set of spindles is disposed.

5. The apparatus of claim 1 further comprising cutting means disposed on said frame for cutting said elastic strand into discrete segments 6. The apparatus of claim 1 further comprising adhesive applying means for applying adhesive to said diaper component web to adhesively unite said elastic strand and said web.

7. The apparatus of claim 6 wherein said adhesive applying means applies adhesive to said web before said transfer means transfers said strand to said web.

8. The apparatus of claim 1 further comprising clamp means disposed on one of said wheels for clamping said strand to said wheel.

9. The apparatus of claim 1 further comprising a supporting roll rotatably mounted on said frame for supporting said web.

10. The apparatus of claim 9 wherein said transfer means includes belt means disposed on said frame for cooperating with said roll to transfer said strand, to adhesively unite said strand to said web, and to apply bond developing pressure to said strand and web.

11. The apparatus of claim 10 wherein said belt means includes a pair of continuous belts disposed at opposite lateral end portions of said supporting roll.

12. Apparatus for applying an elastic waistband in disposable diaper manufacture comprising:
a frame defining a first longitudinally extending path for advancing a diaper component web;
means operably associated with said frame for advancing said component web in said first path;
means operably associated with said frame for applying adhesive to said web at longitudinally spaced portions thereof;
a pair of spaced apart wheels mounted on said frame in said second path prior to the intersection of said paths for rotation about angularly related axes to pass through a first position and a second position spaced from said first position, said second position being at the intersection of said paths;
said wheels each being equipped with spindle mans disposed on the periphery of each of said wheels for receiving an elastic strand and placing said strand into a stretched, sinuous configuration upon wheel rotation from said first to said second position, the spindle means of one wheel interleaving with the spindle means of the other wheel at the first position so that the spindle means may receive the strand at the first position and move adjacent portions of the strand in opposite directions as the wheels rotate away from the first position;
means on said frame in said second path for advancing said elastic strand material toward said wheels;
means operably associated with said frame for rotating said wheels to place said wheel peripheries closer together at said first position than at said second position whereby said elastic strand material is elastically stretched in moving from said first position to said second position; and
transfer means disposed on said frame for removing said elastic strand from said spindle means at a second position, adhesively and substantially simultaneously uniting said elastic strand to a diaper component web, and applying a pressure for a predetermined duration to allow the bond between the elastic strand and the diaper component web to develop.

13. A method of manufacturing disposable diapers using a pair of canted wheels rotated about angularly related axes, said wheels each including spindle means for stretching a strand of elastic material and placing it in a predetermined configuration, said method comprising the steps of:
(a) advancing an elongate diaper component web along a predetermined path;
(b) rotatably advancing an elastic strand material with said canted wheels and spindle means and simultaneously bending said strand into a predetermined configuration and stretching said strand, said spindle means interleaving and receiving the strand at the first position and moving adjacent portions of the strand in opposite directions to form the predetermined configuration;
(c) adhesively uniting said elastic strand and said elongate diaper component web at the second position; and
(d) applying pressure to said elastic strand and said component web for a predetermined duration.

14. The method of claim 13 wherein said elastic strand is placed transversely of said elongate diaper component web.

15. The method of claim 13 wherein steps (c) and (d) are performed while said component web is supported.

* * * * *